United States Patent
Youk et al.

(10) Patent No.: US 11,964,925 B2
(45) Date of Patent: Apr. 23, 2024

(54) METHOD FOR PREPARING OLIGOMER (71) Applicant: LG Chem, Ltd., Seoul (KR)

(72) Inventors: Kyung Seog Youk, Daejeon (KR); Jong Hun Song, Daejeon (KR); Min Ho Sun, Daejeon (KR); Hong Min Lee, Daejeon (KR); Hyun Seok Kim, Daejeon (KR); Moon Sub Hwang, Daejeon (KR); Jeong Seok Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 71 days.

(21) Appl. No.: 17/910,228

(22) PCT Filed: Jan. 10, 2022

(86) PCT No.: PCT/KR2022/000346
§ 371 (c)(1),
(2) Date: Sep. 8, 2022

(87) PCT Pub. No.: WO2022/154398
PCT Pub. Date: Jul. 21, 2022

(65) Prior Publication Data
US 2023/0098226 A1    Mar. 30, 2023

(30) Foreign Application Priority Data

Jan. 18, 2021 (KR) .................. 10-2021-0006655

(51) Int. Cl.
*C07C 2/08* (2006.01)
*B01F 23/00* (2022.01)
(Continued)

(52) U.S. Cl.
CPC .................. *C07C 2/08* (2013.01); *C07C 7/09* (2013.01); *C07C 7/152* (2013.01); *C07C 11/107* (2013.01);
(Continued)

(58) Field of Classification Search
CPC .. C07C 2/08; C07C 7/09; C07C 7/152; C07C 11/107; C07C 7/00; C07C 2531/14;
(Continued)

(56) References Cited

U.S. PATENT DOCUMENTS 4,020,121 A * 4/1977 Kister ................ C07C 2/08
585/521
5,286,806 A   2/1994 Neff et al.
(Continued)

FOREIGN PATENT DOCUMENTS

CN      106029611 A    10/2016
JP      H07149677 A    6/1995
(Continued)

OTHER PUBLICATIONS

Suzuki, Mamoru, "Utilization of Polymer Flocculants" Kobunshi, 1972, vol. 21, No. 11, p. 586-591, doi:10.1295/kobunshi.21.11_586 [English Translation of Abstract only attached].
(Continued)

*Primary Examiner* — Ali Z Fadhel
(74) *Attorney, Agent, or Firm* — Lerner David LLP (57) ABSTRACT

Provided is a method for preparing an oligomer including: supplying a monomer stream and a solvent stream to a reactor to perform an oligomerization reaction to prepare a reaction product; supplying a discharge stream from the reactor including the reaction product to a separation device and supplying a lower discharge stream from the separation device to a settling tank; adding an organic flocculant to the settling tank to settle and remove a polymer and supplying the lower discharge stream from the separation device from which the polymer is removed to a high boiling point separation column; and removing a high boiling point material from the lower portion in the high boiling point sepa-
(Continued)

ration column and supplying an upper discharge stream including an oligomer to a solvent separation column.

14 Claims, 4 Drawing Sheets

(51) Int. Cl.
*B01F 23/70* (2022.01)
*B01F 23/80* (2022.01)
*C07B 63/00* (2006.01)
*C07B 63/02* (2006.01)
*C07B 63/04* (2006.01)
*C07C 7/09* (2006.01)
*C07C 7/152* (2006.01)
*C07C 11/107* (2006.01)

(52) U.S. Cl.
CPC ............. *B01F 23/00* (2022.01); *B01F 23/70* (2022.01); *B01F 23/706* (2022.01); *B01F 23/80* (2022.01); *B01F 23/807* (2022.01); *C07B 63/00* (2013.01); *C07B 63/02* (2013.01); *C07B 63/04* (2013.01)

(58) Field of Classification Search
CPC ........ B01F 23/00; B01F 23/70; B01F 23/706; B01F 23/80; B01F 23/807; C07B 63/00; C07B 63/02; C07B 63/04; B03D 3/00
See application file for complete search history.

(56) References Cited

U.S. PATENT DOCUMENTS

| | | | |
|---|---|---|---|
| 5,750,816 A | 5/1998 | Araki et al. | |
| 6,011,176 A * | 1/2000 | Paulus .................... | C07C 67/58 562/598 |
| 8,524,972 B1 * | 9/2013 | Weber ...................... | C07C 7/04 208/356 |
| 2008/0177012 A1 | 7/2008 | Penzo et al. | |
| 2009/0192342 A1 | 7/2009 | Coupard et al. | |
| 2009/0326297 A1 | 12/2009 | Emoto et al. | |
| 2010/0217058 A1 * | 8/2010 | Fritz ........................ | C07C 2/08 585/520 |
| 2013/0102826 A1 | 4/2013 | Lattner et al. | |
| 2013/0144024 A1 * | 6/2013 | Lattner .................... | B01J 8/005 585/511 |
| 2014/0121435 A1 * | 5/2014 | Zilbershtein .............. | C07C 2/32 585/800 |
| 2016/0362350 A1 | 12/2016 | Toda et al. | |
| 2017/0190637 A1 | 7/2017 | Emoto | |
| 2017/0349509 A1 * | 12/2017 | Zilbershtein ........... | B01J 31/143 |
| 2018/0009728 A1 * | 1/2018 | Emoto ....................... | C08F 6/12 |
| 2018/0044266 A1 | 2/2018 | Jeong et al. | |
| 2018/0354870 A1 * | 12/2018 | Wei .......................... | C07C 2/30 |
| 2020/0055798 A1 * | 2/2020 | Miyamoto ................ | C08F 6/04 |
| 2020/0055799 A1 * | 2/2020 | Nadler ....................... | C07C 2/02 |
| 2020/0055800 A1 * | 2/2020 | Weber ....................... | C07C 2/32 |
| 2020/0062672 A1 * | 2/2020 | Weber ...................... | C08F 10/00 |
| 2020/0062673 A1 * | 2/2020 | Weber ....................... | C08F 2/01 |
| 2021/0009486 A1 * | 1/2021 | Allen ........................ | C07C 2/08 |
| 2021/0230085 A1 | 7/2021 | Kim et al. | |

FOREIGN PATENT DOCUMENTS

| | | |
|---|---|---|
| JP | H11269127 A | 10/1999 |
| JP | 2003096129 A | 4/2003 |
| JP | 2003251107 A | 9/2003 |
| JP | 2006007208 A | 1/2006 |
| JP | 3839818 B2 | 11/2006 |
| JP | 2009504579 A | 2/2009 |
| JP | 5537816 B2 | 7/2014 |
| JP | 2016065051 A | 4/2016 |
| JP | 2018502088 A | 1/2018 |
| JP | 2018080301 A | 5/2018 |
| KR | 20140047665 A | 4/2014 |
| KR | 20160144805 A | 12/2016 |
| KR | 20170058935 A | 5/2017 |
| KR | 20170098282 A | 8/2017 |
| KR | 20180035586 A | 4/2018 |
| KR | 20200070745 A | 6/2020 |
| WO | 2020171730 A1 | 8/2020 |

OTHER PUBLICATIONS

International Search Report for Application No. PCT/KR2022/000346 dated Apr. 25, 2022, pp. 1-4.
Extended European Search Report for Application No. 22739594.4 dated Sep. 27, 2023, pp. 1-5.

* cited by examiner

METHOD FOR PREPARING OLIGOMER

CROSS-REFERENCE TO RELATED APPLICATIONS

The present application is a national stage entry under 35 U.S.C. § 371 of International Application No. PCT/KR2022/000346 filed on Jan. 10, 2022, which claims priority from Korean Patent Application No. 10-2021-0006655 filed on Jan. 18, 2021, all the disclosures of which are incorporated herein by reference.

TECHNICAL FIELD

The present invention relates to a method for preparing an oligomer, and more particularly, to a method for preparing an oligomer, which may efficiently remove polyethylene from an oligomerization reaction product of ethylene and may reduce energy costs for reuse of a solvent.

BACKGROUND ART

An α-olefin (alpha-olefin) is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The α-olefin is prepared, most typically, by an oligomerization reaction of ethylene. As a reactor form in which the oligomerization reaction of ethylene is carried out, a bubble column reactor which performs an oligomerization reaction (trimerization reaction or tetramerization reaction) of ethylene by a contact with a reaction area including a liquid reaction medium including a catalyst, using gaseous ethylene as a reactant, is being used.

In the bubble column reactor, the reaction is carried out by introducing a gaseous reactant to a reaction area including a liquid reaction medium through a porous dispersion plate installed in a lower portion of the reactor and dispersing the reactant simultaneously, and producing turbulence by a dispersed gas force to perform natural mixing.

As a result of the oligomerization reaction, about 0.1 to 5 wt % of a polymer, for example, polyethylene is produced in a small amount as a by-product and floats in a liquid reaction medium, and as time passes, the polymer accumulates in the porous dispersion plate and the inner wall of the reactor by fouling, and thus, operation of the entire process should be shut down and washing should be performed.

Meanwhile, in order to remove the polymer from the oligomerization reaction product and recover an oligomer and a solvent, a high boiling point separation column and a solvent separation column should be operated in a latter stage of the reactor, and as the flow rates supplied to the high boiling point separation column and the solvent separation column are increased, and polyethylene is more included in the reaction product, energy costs and time for separation are increased. In addition, in the process of supplying the oligomerization reaction product from the reactor to the high boiling point separation column or the solvent separation column in the latter stage, a fouling problem of a pump by polyethylene occurs.

DISCLOSURE

Technical Problem

An object of the present invention is to provide a method for reducing energy costs and shortening a separation time, in removing a polymer floating in a reaction product, recovering and reusing a solvent, and separating the oligomer with a high purity during a process of preparing an oligomer, in order to solve the problems mentioned in the Background Art.

Technical Solution

In one general aspect, a method for preparing an oligomer includes: supplying a monomer stream and a solvent stream to a reactor to perform an oligomerization reaction to prepare a reaction product; supplying a discharge stream from the reactor including the reaction product to a separation device and supplying a lower discharge stream from the separation device to a settling tank; adding an organic flocculant to the settling tank to settle and remove a polymer and supplying the lower discharge stream from the separation device from which the polymer is removed to a high boiling point separation column; and removing a high boiling point material from a lower portion in the high boiling point separation column and supplying an upper discharge stream including an oligomer to a solvent separation column.

Advantageous Effects

According to the present invention, a settling tank is introduced to front ends of a high boiling point separation column and a solvent separation column in which a polymer material and a solvent are separated from an oligomerization reaction product, thereby minimizing a flow rate of a reaction product and a polymer content supplied to the high boiling point separation column and the solvent separation column, and thus, time and energy use for separation in the high boiling point separation column and the solvent separation column may be reduced.

In addition, in the present invention, an organic flocculant is added to the settling tank, thereby shortening a time taken to settle and remove a high boiling point material in the settling tank, and thus, shortening a time taken for an entire process of removing a solvent and a by-product from an oligomerization reaction product and obtaining high-purity oligomer.

In addition, in the present invention, an upper layer liquid stream having a high solvent content in the settling tank is directly supplied to a solvent separation column without passing through the high boiling point separation column, thereby decreasing a flow rate of a stream supplied to the high boiling point separation column to further decrease energy use in the high boiling point separation column.

BEST MODE

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "upper portion" means a portion corresponding to a height at or above 50% of the total height of an apparatus or a container, and the term "lower portion" means a portion corresponding to a height less than 50% of the total height of an apparatus or in a container.

In the present invention, the term "stream" may refer to a fluid flow in the process, or may refer to the fluid itself flowing in a moving line (pipe). Specifically, the "stream" may refer to both a fluid itself flowing in a pipe connecting each device and a fluid flow. In addition, the fluid may refer to inclusion of any one or more of gas, liquid, and solid.

In the present invention, the term "C#" in which "#" is a positive integer represents all hydrocarbons having # carbon atoms. Therefore, the term "010" represents a hydrocarbon compound having 10 carbon atoms. In addition, the term "C#+" represents all hydrocarbon molecules having # or more carbon atoms. Therefore, the term "C10+" represents a mixture of hydrocarbons having 10 or more carbon atoms.

Hereinafter, the present invention will be described in more detail referring to the following FIGS. 1 and 2, for better understanding of the present invention.

According to an exemplary embodiment of the present invention, a method for preparing an oligomer is provided. The method for preparing an oligomer may include: supplying a monomer stream and a solvent stream to a reactor 100 to perform an oligomerization reaction to prepare a reaction product; supplying a discharge stream from the reactor 100 including the reaction product to a separation device 200 and supplying a lower discharge stream from the separation device 200 to a settling tank 300; adding an organic flocculant to the settling tank 300 to settle and remove a polymer and supplying the lower discharge stream from the separation device from which the polymer is removed to a high boiling point separation column 400; and removing a high boiling point material from a lower portion in the high boiling point separation column and supplying an upper discharge stream including an oligomer to a solvent separation column 500.

According to an exemplary embodiment of the present invention, a monomer stream and a solvent stream may be supplied to a reactor 100 and subjected to an oligomerization reaction to prepare a reaction product.

The reactor 100 may be a reactor for oligomerizing a monomer in the presence of a catalyst and a solvent to prepare an oligomer. For example, the reactor 100 may be a reactor appropriate for a continuous process, and may include one or more reactors selected from the group consisting of a continuous stirred-tank reactor, a plug flow reactor, and a bubble column reactor. Thus, an oligomer product may be continuously prepared.

In addition, the monomer may include ethylene. Specifically, a monomer stream including an ethylene monomer may be supplied to the reactor 100 to prepare an α-olefin as a desired oligomer by an oligomerization reaction. Here, the oligomerization reaction is carried out in a reaction medium in a lower to middle area of the reactor 100, and the oligomerization reaction of the monomer may be carried out in a liquid state dissolved in a solvent in the presence of a catalyst and a cocatalyst. The oligomerization reaction may refer to a reaction in which a monomer is oligomerized. The oligomerization may be referred to as trimerization or tetramerization depending on the number of monomers to be polymerized, and these are collectively called multimerization.

The α-olefin, which is an important material used in copolymers, cleaning agents, lubricants, plasticizers, and the like, is commercially widely used, and in particular, 1-hexene and 1-octene are often used as a comonomer for adjusting the density of polyethylene in the preparation of linear low-density polyethylene (LLDPE). The α-olefin such as 1-hexene and 1-octene may be prepared by, for example, a trimerization reaction or tetramerization reaction of ethylene.

The oligomerization reaction of the monomer may be carried out by a homogeneous liquid phase reaction, a slurry reaction in which the catalyst is in the form of being partially not dissolved or completely not dissolved, a two-phase liquid/liquid reaction, or a bulk phase reaction or gas phase reaction of which the product acts as a main medium, in the presence or absence of a solvent, by applying the reaction system and a common contact technology.

The catalyst may include a transition metal source. The transition metal source may be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafloro-2,4-pentanedionate, chromium (III) acetate hydroxide, chromium (III) acetate, chromium (III) butyrate, chromium (III) pentanoate, chromium (III) laurate, and chromium (III) stearate.

The cocatalyst may include, for example, one or more selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, modified methylaluminoxane, and borate.

As such, in the process of oligomerizing a monomer in the presence of a catalyst and a solvent, a polymer such as polyethylene may be produced as a by-product, in addition to an oligomer product. The polymer floats in a liquid reaction medium in the reactor, and as time passes, a problem in which the polymer is accumulated in an inner wall and a porous plate of the reactor to a certain thickness due to a fouling phenomenon arises. In this case, since operation of the reactor should be shut down, there is a problem of increased costs required in a washing process as well as a problem of decreased production due to a decreased operation time.

In addition, a high boiling point separation column 400 and a solvent separation column 500 should be provided in order to remove a polymer in the reaction product, and to recover and reuse a solvent used in a large amount as compared with a reactant. Here, as a stream flow rate and a polymer content supplied to the high boiling point separation column 400 and the solvent separation column 500 are higher, energy costs and time for separation are increased.

In this regard, in the present invention, in order to remove the polymer in the reaction product, a settling tank 300 is provided in front ends of the high boiling point separation column 400 and the solvent separation column 500, thereby reducing energy costs used for separation in the high boiling point separation column 400 and the solvent separation column 500 and shortening time, and thus, the problems described above were solved.

In addition, an organic flocculant is added to the settling tank 300 to settle and remove a polymer, thereby shortening a time taken to settle and remove a high boiling point material in the settling tank 300, and thus, shortening a time taken for an entire process of removing a solvent and a by-product from an oligomerization reaction product and obtaining a high-purity oligomer. For example, the organic flocculant may be supplied into the settling tank 300 through a separate flocculant supply line 310 provided by being connected to the settling tank 300.

Besides, an upper layer liquid stream having a high solvent content in the settling tank 300 is supplied directly to the solvent separation column 500 without passing through the high boiling point separation column 400, thereby lowering a flow rate supplied to the high boiling point separation column 400 to further reduce energy use in the high-point separation column 400.

The monomer stream may be supplied to the reactor 100 through a monomer stream supply line provided in a lower portion of the reactor 100. Here, the monomer may be supplied in a gaseous state to the reactor 100. Specifically, the monomer stream including a gaseous monomer may be supplied to the reactor 100, and the gaseous monomer may be dissolved in a solvent supplied to the reactor 100 to carry out the oligomerization reaction in a liquid phase.

The monomer stream may be supplied from a naphtha cracking center (NCC). In the naphtha cracking center, a process including: adding each of naphtha, C2 and C3 hydrocarbon compounds, propane, and the like as a supply raw material and carrying out cracking in each pyrolysis furnace; cooling cracking gas which has been pyrolyzed in each pyrolysis furnace to include hydrogen, and C1, C2, and C3 or higher hydrocarbon compounds; compressing the cooled cracking gas; and purifying a cracking compression stream including hydrogen, and C1, C2, and C3 or higher hydrocarbon compounds, may be carried out. Here, the monomer stream may be a stream including an ethylene monomer (C2) separated from naphtha cracking.

The solvent stream may be supplied to the reactor 100 through a solvent stream supply line provided in a lower side of the reactor 100. The solvent may include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. The solvent may be used in combination of two or more, if necessary. Thus, a gaseous ethylene monomer may be liquefied at a higher temperature and a dissolution rate at which the gaseous ethylene monomer is dissolved in the solvent may be improved.

The oligomerization reaction which is carried out in the reactor 100 by supplying a monomer stream and a solvent stream thereto may be carried out at a temperature of 10° C. to 180° C., 30° C. to 150° C., or 50° C. to 120° C. In addition, the oligomerization reaction may be carried out under a pressure of 10 bar·g to 70 bar·g. For example, the oligomerization reaction may be carried out under a pressure of 10 bar·g to 70 bar·g, 20 bar·g to 65 bar·g, or 20 bar·g to 40 bar·g. When ethylene is oligomerized within the temperature range and the pressure range, a selectivity to a desired α-olefin may be excellent, a by-product amount may be decreased, an operational efficiency of a continuous process may be increased, and costs may be reduced.

By-products produced in the oligomerization reaction in the reactor 100, for example, the polymer may be included at a content of 0.1 wt % to 5 wt %, 0.1 wt % to 4 wt %, or 1 wt % to 3 wt % in a discharge stream from the reactor 100.

The discharge stream from the reactor 100 may include a liquid first stream and a gaseous second stream. For example, in the reactor 100, a liquid reaction product including a desired oligomer product by the oligomerization reaction may be discharged through a product discharge line provided in a spaced state in a direction opposite to a lower side of the reactor 100, for example, a lower side of the reactor 100 where the solvent supply line is formed, as the first stream. For example, the product discharge line may be formed at the same height as the solvent supply line. In addition, the product discharge line from the reactor 100 is connected to a separation device 200 and may transfer a reaction product to the separation device 200.

In addition, the second stream including a gaseous unreacted monomer which is not dissolved in a solvent and does not participate in the oligomerization reaction in the reactor 100 may be discharged through an unreacted monomer discharge line provided in an upper portion of the reactor 100. For example, the gaseous second stream passes through a condenser 110 and is condensed into a liquid phase, and may be supplied to the separation device 200 with the first stream. Here, the first stream and the second stream may be supplied to the separation device 200 through a separate line or may be joined as one line and supplied to the separation device 200.

According to an exemplary embodiment of the present invention, the discharge stream from the reactor 100 is supplied to the separation device 200 in which the unreacted monomers and dimers in the reaction product may be separated. Specifically, in the separation device 200, the unreacted monomers and dimers are separated as an upper discharge stream from the discharge stream from the reactor 100 including the reaction product supplied and is circulated to the reactor 100 for reuse. Here, the upper discharge stream from the separation device 200 may pass through the compressor 210 for securing flowability to the reactor 100 and be circulated to the reactor 100. In addition, the lower discharge stream from the separation device 200 may be supplied to a settling tank 300 as the reaction product from which most unreacted monomers are removed.

An operation temperature and an operation pressure of the separation device 200 may be controlled for selectively separating a low boiling point material including monomers and dimers to the upper portion. For example, the operation temperature of the separation device 200 may be 20° C. to 250° C., 30° C. to 200° C., or 40° C. to 160° C., and the operation pressure of the separation device 200 may be 10 bar·g to 30 bar·g, 10 bar·g to 25 bar·g, or 10 bar·g to 20 bar·g.

According to an exemplary embodiment of the present invention, the lower discharge stream from the separation device 200 is supplied to the settling tank 300, and the polymer in the reaction product may be removed in the settling tank 300. Specifically, in the settling tank 300, the polymer floating in the reaction product may be settled as an aggregate and be discharged to a lower portion of the settling tank 300, and then may be discarded or reused in various routes.

To the settling tank 300, an organic flocculant may be added. Specifically, a process of settling and removing the polymer in the reaction product in the settling tank 300 may be carried out in the presence of the organic flocculant. Thus, a time taken to settle and remove the high boiling point material in the settling tank 300 may be shortened, and accordingly, a time taken for an entire process of removing a solvent and a by-product from an oligomerization reaction product and obtaining high-purity oligomer may be shortened. In addition, the content of the polymer in addition to the solvent in the upper layer liquid in the settling tank 300 is minimized, thereby supplying an upper layer liquid stream including a high-purity solvent to a solvent separation column 500 through a solvent extraction line 320 described later, and thus, further reducing energy costs used for separation in the solvent separation column 500.

The organic flocculant may include, for example, polyacrylamide. The polyacrylamide is a non-ionic flocculant, and may derive coarsening, that is, flocculation of solid particles by crosslinking by physical or chemical adsorption between the surface of the solid particles suspended in a liquid and the flocculant. As such, the aggregate formed by flocculating the solid particles may accelerate a settling rate to promote settling. That is, according to the present invention, the polyacrylamide may have an excellent effect of flocculating solid particles of polyethylene dispersed in the reaction product to form an aggregate, thereby promoting settling.

Specifically, the settling tank 300 is operated under the conditions of adding the organic flocculant to settle and remove the polymer in the reaction product, thereby shortening the operating time of the settling tank 300. For example, the lower discharge stream from the separation device stands in the settling tank for 1 hour or less, 40 minutes or less, or 1 minute to 10 minutes.

The operating temperature and the operating pressure of the settling tank 300 may be controlled for settling and removing the polymer in the reaction product. For example, the operating temperature of the settling tank 300 may be controlled to 10° C. to 90° C., 10° C. to 85° C., or 20° C. to 80° C., and the operating pressure of the settling tank 300 may be controlled to 0.1 kg/cm$^2$ to 3 kg/cm$^2$, 0.5 kg/cm$^2$ to 2 kg/cm$^2$, or 0.5 kg/cm$^2$ to 1.5 kg/cm$^2$. Here, the operating pressure of the settling tank 300 may be controlled using an inert gas. The inert gas may include one or more selected from the group consisting of nitrogen ($N_2$) and argon (Ar), and as a specific example, the inert gas may be nitrogen ($N_2$).

As such, in the settling tank 300, polyacrylamide is used as an organic flocculant and also the operating temperature and the operating pressure are controlled as described above, thereby maximizing a flocculating and settling effect of the polymer included in the lower discharge stream from the separation device 200. As a specific example, the polymer may have a weight average molecular weight of 80,000 to 150,000 g/mol, 90,000 to 130,000 g/mol, or 90,000 to 120,000 g/mol. When for the polymer having the weight average molecular weight within the range, polyacrylamide is used as the organic flocculant and the operating temperature and the operating pressure are controlled as described above, the flocculating and settling effect is improved to shorten an operating time of the settling tank 300 as much as possible.

Also, in the process of removing the polymer in the reaction product in the settling tank 300, layer separation into an upper layer liquid having a high solvent content and a lower layer liquid having a high oligomer content may be performed in the settling tank 300. The upper layer liquid separated in the settling tank 300, which has a high solvent content and contains almost no impurities other than the solvent, may be directly supplied to a solvent separation column 500, without being supplied to the high boiling point separation column 400. Here, the solvent content in the upper layer liquid in the settling tank 300 may be 90 wt % or more, 90 wt % to 100 wt %, or 95 wt % to 100 wt %. As such, in the settling tank 300, the polymer is removed while the upper layer liquid containing almost no impurities other than the solvent is directly supplied to the solvent separation column 500 without passing through the high boiling point separation column 400, thereby decreasing a flow rate supplied to the high boiling point separation column 400 to reduce energy costs for separation in the high boiling point separation column 400.

The upper layer liquid and the lower layer liquid which are separated in the settling tank 300 may be different depending on the contents of the solvent and the oligomer included in the lower discharge stream from the separation device 200, and in order to supply the upper layer liquid stream to the solvent separation column 500, a solvent extraction line 320 connected from the solvent separation column 500 and extended to an area in the settling tank 300 where the upper layer liquid is formed may be further provided. Here, a pump 330 is installed in an arbitrary area of the solvent extraction line 320 to transfer the upper layer liquid stream from the settling tank 300 to the solvent separation column 500.

In addition, the lower layer liquid stream from the settling tank 300 has a high oligomer content and may be supplied to the high boiling point separation column 400. Here, the polymer content in the lower layer liquid stream in the settling tank 300 may be 10 wt % or less, 0.1 wt % to 5 wt %, or 0.1 wt % to 3 wt %. In addition, a ratio of the polymer content in the lower layer liquid stream in the settling tank 300 to the polymer content in the discharge stream from the reactor 100 may be 1:0.01 to 1:0.05, 1:0.01 to 1:0.04, or 1:0.01 to 1:0.03. This means that 95% or more of the polymer included in the discharge stream from the reactor 100 is removed from the settling tank 300, from which it is found that energy costs required in the separation in the solvent separation column 500 together with the high boiling point separation column 400 may be reduced and a time therefor may be shortened.

According to an exemplary embodiment of the present invention, the lower layer liquid stream from the settling tank 300 is supplied to the high boiling point separation column 400 and the high boiling point material included in the lower layer liquid stream from the settling tank 300 may be removed by distillation in the high boiling point separation column 400. Here, since only the lower layer liquid of the settling tank 300 is supplied to the high boiling point separation column 400, a flow rate supplied to the high boiling point separation column 400 is decreased, and since the polymer content in the lower layer liquid is low, energy costs for separation in the high boiling point separation column 400 may be reduced and separation time may be shortened.

In addition, in the high boiling point separation column 400, the high boiling point material is removed from a lower portion of the high boiling point separation column through the lower discharge stream, and the remaining components, that is, the upper discharge stream having a high oligomer content may be supplied to the solvent separation column 500 to purify the oligomer.

According to an exemplary embodiment of the present invention, in the solvent separation column 500, the solvent and the oligomer may be separated by a boiling point difference between the solvent and the oligomer. Specifically, the upper layer liquid stream of the settling tank 300 and the upper discharge stream from the high boiling point separation column 400 are supplied to the solvent separation column 500 and may be separated into the solvent and the oligomer in the solvent separation column 500. Here, when the oligomer includes two or more oligomers having different boiling points, two or more solvent separation columns 500 may be provided. For example, when two or more having different boiling points are included, a higher boiling point oligomer is separated in a first solvent separation column and the solvent and a lower boiling point oligomer may be separated in a second solvent separation column.

A solvent stream separated in the solvent separation column 500 is discharged to a lower portion of the solvent separation column 500, which may be circulated to the reactor 100 and reused. Thus, raw material costs may be reduced to lower a unit cost of the oligomer product, thereby securing competitiveness.

According to an exemplary embodiment of the present invention, in the method for preparing an oligomer, if necessary, devices such as a distillation column, a condenser, a reboiler, a valve, a pump, a separator, and a mixer may be further installed.

Hereinabove, the method for preparing an oligomer according to the present invention has been described and illustrated in the drawings, but the description and the illustration in the drawings are the description and the illustration of only core constitutions for understanding of the present invention, and in addition to the processes and devices described above and illustrated in the drawings, the processes and the devices which are not described and illustrated separately may be appropriately applied and used for carrying out the method for preparing an oligomer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

Figure 1:
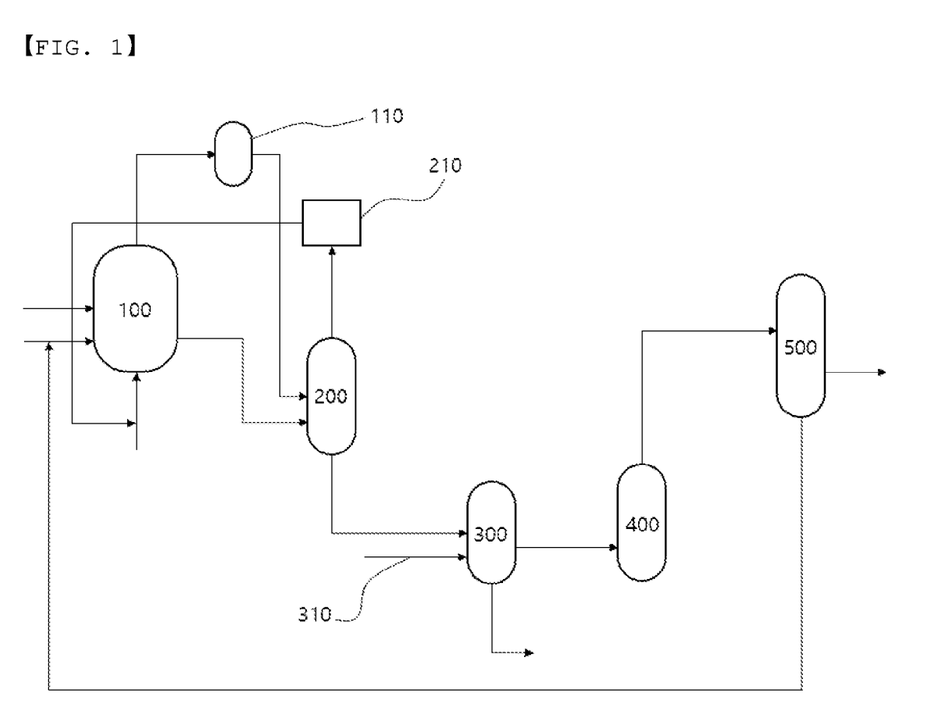
FIGS. 1 and 2 are process flow diagrams of a method for preparing an oligomer according to an exemplary embodiment of the present invention, respectively.

According to the process flow diagram illustrated in FIG. 1, an α-olefin was prepared.

Specifically, a gaseous ethylene monomer stream was supplied at 113 kg/hr to a lower portion of the reactor 100, methylcyclohexane was supplied at 7 kg/hr to a lower side thereof, and a catalyst and a cocatalyst were supplied thereto, thereby performing an oligomerization reaction of an ethylene monomer to produce a reaction product including an α-olefin as an oligomer. Here, a polymer content included in the reaction product was confirmed to be 1.9 wt %, and the temperature and the pressure of the reactor 100 were set to 70° C. and 40 bar·g, respectively.

A discharge stream from the reactor 100 was supplied to the separation device 200. Specifically, a gaseous second stream was condensed into a liquid phase by the condenser 110 and then supplied to the separation device 200, and a liquid first stream was directly supplied to the separation device 200.

An upper discharge stream from the separation device 200 including a gaseous unreacted monomer passed through the compressor 210 and was supplied to the reactor 100, and a lower discharge stream was supplied to the settling tank 300.

In the settling tank 300, the lower discharge stream from the separation device 200 was allowed to stand for 20 minutes in a state of controlling the amount of polyacrylamide (PAA) added through a flocculant supply line 310 to 0.1 kg, the operating temperature to 20° C., and the operating pressure to 1 kg/cm², thereby performing layer separation. At this time, the settled polymer was discharged to a lower portion and removed and an upper layer liquid and a lower layer liquid were supplied to a high boiling point separation column 400 at a flow rate of 6.5 kg/hr. At this time, it was confirmed that a solvent content in the upper layer liquid was 99 wt % and a polymer content in the lower layer liquid was 0.25 wt %.

In the high boiling point separation column 400, a high boiling point material was removed in a lower portion and an upper discharge stream was supplied to a solvent separation column 500, and in the solvent separation column 500, an α-olefin which is an oligomer was recovered in a side portion and a lower discharge stream was circulated to the reactor 100.

Example 2

Figure 2:
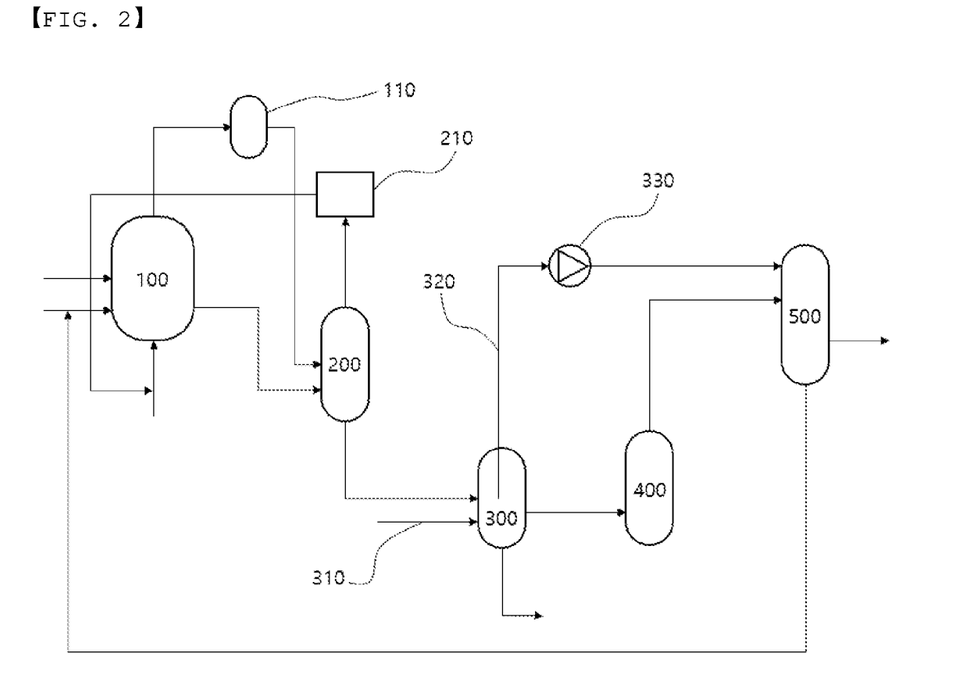

According to the process flow diagram illustrated in FIG. 2, an α-olefin was prepared.

Specifically, the process was performed in the same manner as in Example 1, except that the settled polymer settled in the settling tank 300 was discharged to a lower portion and removed, a upper layer liquid having a solvent content of 99 wt % was supplied to the solvent separation column 500 using a pump 330 through a solvent extraction line 320 at a flow rate of 3.0 kg/hr, and a lower layer liquid having a polymer content of 0.25 wt % was supplied to the high boiling point separation column 400 at a flow rate of 3.5 kg/hr.

Example 3

The process was performed in the same manner as in Example 2, except that the settling tank 300 was operated for 40 minutes while the operating temperature of the settling tank 300 was controlled to 40° C., thereby performing layer separation.

At this time, in the settling tank 300, the settled polymer was discharged to a lower portion and removed, an upper layer liquid having a solvent content of 98 wt % was supplied to the solvent separation column 500 using a pump 330 through a solvent extraction line 320 at a flow rate of 3.0 kg/hr, and a lower layer liquid having a polymer content of 0.34 wt % was supplied to the high boiling point separation column 400 at a flow rate of 3.5 kg/hr.

Example 4

The process was performed in the same manner as in Example 3, except that 0.5 kg of polyacrylamide (PAA) was added to the settling tank 300 and the settling tank was operated for 10 minutes to perform layer separation.

At this time, in the settling tank 300, the settled polymer was discharged to a lower portion and removed, an upper layer liquid having a solvent content of 99 wt % was supplied to the solvent separation column 500 using a pump 330 through a solvent extraction line 320 at a flow rate of 3.0 kg/hr, and a lower layer liquid having a polymer content of 0.22 wt % was supplied to the high boiling point separation column 400 at a flow rate of 3.5 kg/hr.

Example 5

The process was performed in the same manner as in Example 3, except that 1.0 kg of polyacrylamide (PAA) was added to the settling tank 300 and the settling tank was operated for 6 minutes to perform layer separation.

At this time, in the settling tank 300, the settled polymer was discharged to a lower portion and removed, an upper layer liquid having a solvent content of 99 wt % was supplied to the solvent separation column 500 using a pump 330 through a solvent extraction line 320 at a flow rate of 3.0 kg/hr, and a lower layer liquid having a polymer content of 0.21 wt % was supplied to the high boiling point separation column 400 at a flow rate of 3.5 kg/hr.

Example 6

The process was performed in the same manner as in Example 2, except that the settling tank 300 was operated for 38 minutes while the operating temperature of the settling tank 300 was controlled to 80° C., thereby performing layer separation.

At this time, in the settling tank 300, the settled polymer was discharged to a lower portion and removed, an upper layer liquid having a solvent content of 98 wt % was supplied to the solvent separation column 500 using a pump 330 through a solvent extraction line 320 at a flow rate of 3.0 kg/hr, and a lower layer liquid having a polymer content of 0.36 wt % was supplied to the high boiling point separation column 400 at a flow rate of 3.5 kg/hr.

Referring to Examples 1 to 6, in the settling tank 300, polyacrylamide as the organic flocculant was added to remove the polymer in the oligomerization reaction product, thereby minimizing a polymer content in the stream transferred to the process in the latter stage within a short time. Thus, it was found that time and energy for separation in the high boiling point separation column 400 and the solvent separation column 500 which are devices in the latter stage were reduced.

In particular, in Examples 2 to 6 in which in the settling tank 300, the upper layer liquid having a high solvent content was transferred to the solvent separation column 500 using a separate solvent extraction line 320 and the lower layer liquid is transferred to the high boiling point separation column 400, it was found that the flow rate transferred to the high boiling point separation column 400 was decreased to further reduce the time and energy for separation.

COMPARATIVE EXAMPLES

Comparative Example 1

Figure 3:
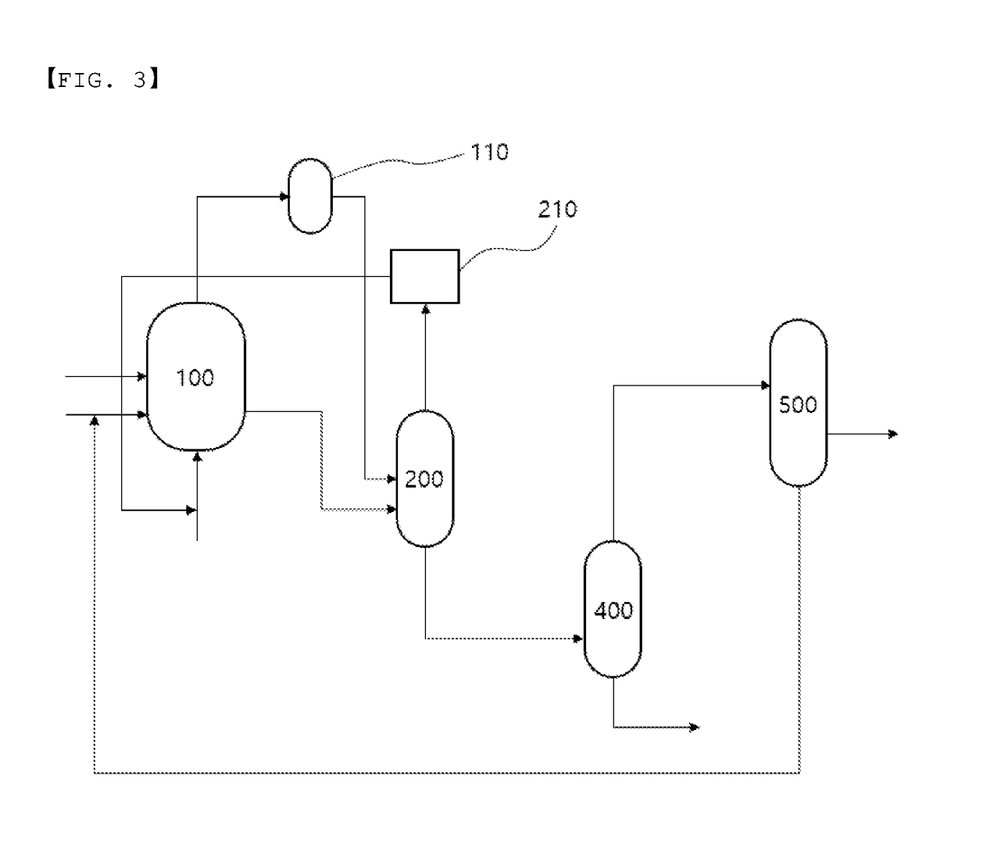
FIGS. 3 and 4 are process flow diagrams of a method for preparing an oligomer according to the comparative examples, respectively.

According to the process flow diagram illustrated in FIG. 3, an α-olefin was prepared.

Specifically, a gaseous ethylene monomer stream was supplied at 113 kg/hr to a lower portion of the reactor 100, methylcyclohexane was supplied at 7 kg/hr to a lower side thereof, and a catalyst and a cocatalyst were supplied thereto, thereby performing an oligomerization reaction of an ethylene monomer to produce a reaction product including an α-olefin as an oligomer. Here, a polymer content included in the reaction product was confirmed to be 1.9 wt %, and the temperature and the pressure of the reactor 100 were set to 70° C. and 40 bar·g, respectively.

A discharge stream from the reactor 100 was supplied to the separation device 200. Specifically, a gaseous second stream was condensed into a liquid phase by the condenser 110 and then supplied to the separation device 200, and a liquid first stream was directly supplied to the separation device 200.

The upper discharge stream from the separation device 200 including a gaseous unreacted monomer passed through a compressor 210 and was supplied to the reactor 100, and a lower discharge stream having a polymer content of 2.2 wt % was supplied to the high boiling point separation column 400 at a flow rate of 10 kg/hr.

In the high boiling point separation column 400, a high boiling point material was removed in a lower portion and an upper discharge stream was supplied to a solvent separation column 500, and in the solvent separation column 500, an α-olefin which is an oligomer was recovered in a side portion and a lower discharge stream was circulated to the reactor 100.

Comparative Example 2

Figure 4:
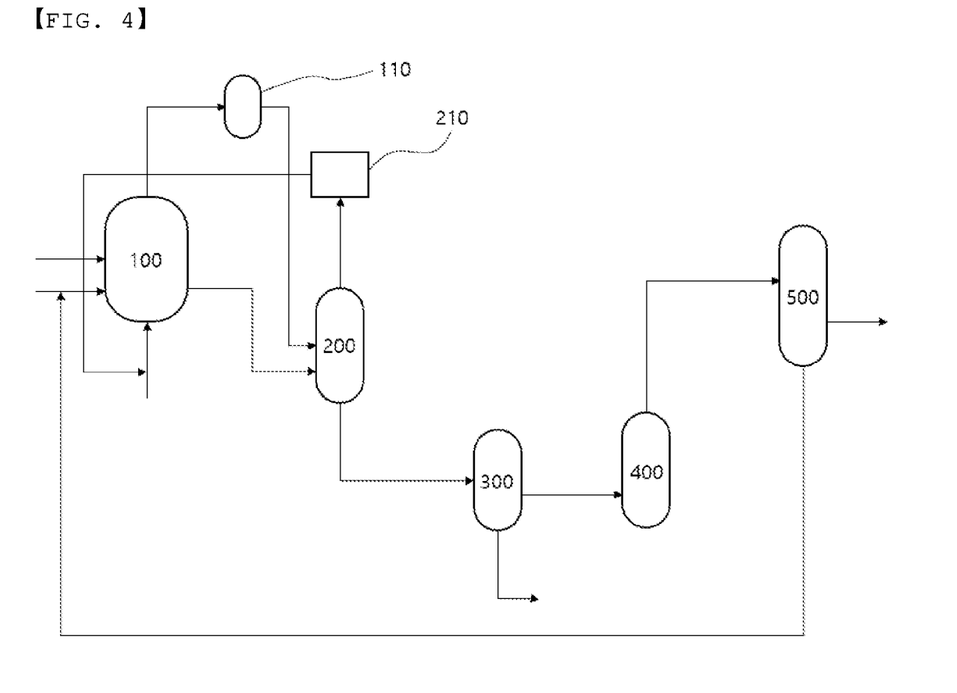

According to the process flow diagram illustrated in FIG. 4, an α-olefin was prepared.

Specifically, a gaseous ethylene monomer stream was supplied at 113 kg/hr to a lower portion of the reactor 100, methylcyclohexane was supplied at 7 kg/hr to a lower side thereof, and a catalyst and a cocatalyst were supplied thereto, thereby performing an oligomerization reaction of an ethylene monomer to produce a reaction product including an α-olefin as an oligomer. Here, a polymer content included in the reaction product was confirmed to be 1.9 wt %, and the temperature and the pressure of the reactor 100 were set to 70° C. and 40 bar·g, respectively.

A discharge stream from the reactor 100 was supplied to the separation device 200. Specifically, a gaseous second stream was condensed into a liquid phase by the condenser 110 and then supplied to the separation device 200, and a liquid first stream was directly supplied to the separation device 200.

An upper discharge stream from the separation device 200 including a gaseous unreacted monomer passed through the compressor 210 and was supplied to the reactor 100, and a lower discharge stream was supplied to the settling tank 300.

The settling tank 300 was operated for 2 hours under the conditions in which the operating temperature was 20° C. and the operating pressure was 1 kg/cm², to perform layer separation of the lower discharge stream from the separation device 200. At this time, the settled polymer was discharged to a lower portion and removed, and an upper layer liquid and a lower layer liquid were supplied to the high boiling point separation column 400 at a flow rate of 6.5 kg/hr. At this time, it was confirmed that a solvent content in the upper layer liquid was 97 wt % and a polymer content in the lower layer liquid was 1.4 wt %.

In the high boiling point separation column 400, a high boiling point material was removed in a lower portion and an upper discharge stream was supplied to a solvent separation column 500, and in the solvent separation column 500, an α-olefin which is an oligomer was recovered in a side portion and a lower discharge stream including the solvent was circulated to the reactor 100.

Comparative Example 3

The process was performed in the same manner as in Comparative Example 2, except that the settling tank 300 was operated for 2 hours while the operating temperature of the settling tank 300 was controlled to 40° C., thereby performing layer separation.

Here, it was confirmed that a solvent content in the upper layer liquid was 95 wt % and a polymer content in the lower layer liquid was 1.9 wt % in the settling tank 300.

Comparative Example 4

The process was performed in the same manner as in Comparative Example 2, except that the settling tank 300 was operated for 2 hours while the operating temperature of the settling tank 300 was controlled to 80° C., thereby performing layer separation.

At this time, it was confirmed that a solvent content in the upper layer liquid was 92 wt % and a polymer content in the lower layer liquid was 2.3 wt % in the settling tank 300.

Comparative Example 5

The process was performed in the same manner as in Comparative Example 2, except that the settling tank 300 was operated for 20 minutes to perform layer separation.

At this time, it was confirmed that a solvent content in the upper layer liquid was 73 wt % and a polymer content in the lower layer liquid was 8.1 wt % in the settling tank 300.

In Comparative Example 1 in which the oligomer was prepared without providing the settling tank, it was found that the flow rate of the stream and the polymer content supplied to the high boiling point separation column 400 were increased as compared with Examples 1 to 6 and Comparative Examples 2 to 5, and thus, time and energy for separation in the high boiling point separation column 400 and the solvent separation column 500 were greatly increased.

Referring to Comparative Examples 2 to 5, it was confirmed that in the settling tank 300, when the organic flocculant was not added thereto, it was difficult to effectively remove the polymer in the oligomerization reaction like the examples, even with the layer separation for 2 hours. Accordingly, it was found that time and energy for separation in the high boiling point separation column 400 and the solvent separation column 500 which are devices in the latter stage were increased. In particular, in Comparative Example 4 in which the settling tank was operated for 20 minutes as in Example 1, it was confirmed that the solvent purity in the upper layer liquid was significantly low and the polymer content in the lower layer liquid was very high. Accordingly, it was difficult to expect the operating time shortening and energy reduction effects for separation in the device in the latter stage from Comparative Examples 1 to 4, which may be obtained in the examples.

In addition, when the upper layer liquid of the settling tank 300 was transferred to the solvent separation column 500 using a separate solvent extraction line 320 in a state in which polymer removal and layer separation were not sufficiently performed, a large amount of impurities were included in the upper layer liquid and a polymer content in the lower layer liquid was high, and thus, the operating time shortening and energy use reduction effects for separation in the high boiling point separation column 400 and the solvent separation column 500 were not shown, and also, the quality of oligomer may be deteriorated.

The invention claimed is:

1. A method for preparing an oligomer, the method comprising:
  supplying a monomer stream comprising a monomer and a solvent stream comprising a solvent to a reactor to perform an oligomerization reaction to prepare a reaction product;
  supplying a discharge stream from the reactor to a separation device, wherein the discharge stream comprises the reaction product, and supplying a lower discharge stream from the separation device to a settling tank;
  adding an organic flocculant to the settling tank to settle and remove a polymer from the lower discharge stream and supplying the lower discharge stream from which the polymer is removed to a high boiling point separation column; and
  removing a high boiling point material from a lower portion in the high boiling point separation column and supplying an upper discharge stream including an oligomer to a solvent separation column.

2. The method for preparing an oligomer of claim 1, wherein the organic flocculant is polyacrylamide.

3. The method for preparing an oligomer of claim 1, wherein the polymer has a weight average molecular weight (Mw) of 80,000 to 150,000 g/mol.

4. The method for preparing an oligomer of claim 1, wherein the lower discharge stream from the separation device stands in the settling tank is for 1 hour or less.

5. The method for preparing an oligomer of claim 1, wherein the lower discharge stream from the separation device stands in the settling tank is for 40 minutes or less.

6. The method for preparing an oligomer of claim 1, wherein an operating temperature of the settling tank is 10° C. to 90° C., and an operating pressure of the settling tank is 0.1 kg/cm$^2$ to 3 kg/cm$^2$.

7. The method for preparing an oligomer of claim 1, wherein the oligomer from which the solvent is separated is obtained in the solvent separation column.

8. The method for preparing an oligomer of claim 1, wherein the monomer includes an ethylene monomer, the oligomer includes an α-olefin, and the polymer includes polyethylene.

9. The method for preparing an oligomer of claim 1, wherein the monomer comprises a α-olefin.

10. A method for preparing an oligomer, the method comprising:
  supplying a monomer stream comprising a monomer and a solvent stream comprising a solvent to a reactor to perform an oligomerization reaction to prepare a reaction product;
  supplying a discharge stream from the reactor to a separation device, wherein the discharge stream comprises the reaction product, and supplying a lower discharge stream from the separation device to a settling tank;
  adding an organic flocculant to the settling tank to settle and remove a polymer from the lower discharge stream, wherein in the settling tank, the lower discharge stream from which the polymer is removed is separated into an upper layer liquid including a solvent and a lower layer liquid including the oligomer, and
  supplying an upper layer liquid stream comprising the solvent to a solvent separation column and a lower layer liquid stream comprising the oligomer to a high boiling point separation column; and
  removing a high boiling point material from a lower portion in the high boiling point separation column and supplying an upper discharge stream including the oligomer to the solvent separation column.

11. The method for preparing an oligomer of claim 10, wherein a solvent extraction line connected from the solvent separation column and extended to an area in the settling tank where the upper layer liquid is formed is further included, and the upper layer liquid stream from the settling tank is supplied to the solvent separation column through the solvent extraction line.

12. The method for preparing an oligomer of claim 10, wherein a solvent content in the upper layer liquid in the settling tank is 90 wt % or more.

13. The method for preparing an oligomer of claim 10, wherein the oligomer from which the solvent is separated is obtained in the solvent separation column.

14. The method for preparing an oligomer of claim 10, wherein the monomer includes an ethylene monomer, the oligomer includes an α-olefin, and the polymer includes polyethylene.

* * * * *